United States Patent
Fujii

(10) Patent No.: US 6,827,709 B2
(45) Date of Patent: *Dec. 7, 2004

(54) MIXING/CHARGING PORT FOR MEDICAL TREATMENT

(75) Inventor: Ryoji Fujii, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/963,835

(22) Filed: Sep. 25, 2001

(65) Prior Publication Data

US 2002/0038107 A1 Mar. 28, 2002

(30) Foreign Application Priority Data

Sep. 26, 2000 (JP) .......................................... 2000-292022

(51) Int. Cl.[7] .............................................. A61M 5/00
(52) U.S. Cl. .......................... 604/256; 604/86; 604/905; 251/149.1
(58) Field of Search ............................... 604/82, 86–88, 604/244, 249, 256, 537, 538, 534, 535, 533, 905, 246, 167.01, 167.02, 167.04, 200–202, 205, 206

(56) References Cited

U.S. PATENT DOCUMENTS

| | | | | |
|---|---|---|---|---|
| 4,981,140 A | * | 1/1991 | Wyatt | 600/486 |
| 5,135,489 A | * | 8/1992 | Jepson et al. | 604/48 |
| 5,178,607 A | * | 1/1993 | Lynn et al. | 604/86 |
| 5,199,948 A | | 4/1993 | McPhee | |
| 5,203,775 A | | 4/1993 | Frank et al. | |
| 5,279,571 A | | 1/1994 | Larkin | |
| 5,306,265 A | * | 4/1994 | Ragazzi | 604/539 |
| 5,324,256 A | * | 6/1994 | Lynn et al. | 604/540 |
| 5,417,673 A | | 5/1995 | Gordon | |
| 5,531,672 A | * | 7/1996 | Lynn | 604/6.12 |
| 5,603,706 A | * | 2/1997 | Wyatt et al. | 604/539 |
| 5,989,216 A | * | 11/1999 | Johnson et al. | 604/288.02 |
| 6,213,973 B1 | * | 4/2001 | Eliasen et al. | 604/93.01 |
| 6,468,251 B1 | | 10/2002 | Yamanaka et al. | |
| 2002/0038106 A1 | * | 3/2002 | Fujii | 604/256 |
| 2002/0038108 A1 | * | 3/2002 | Fujii | 604/256 |

FOREIGN PATENT DOCUMENTS

| | | |
|---|---|---|
| EP | 0 499 401 A | 8/1992 |
| EP | 0 783 899 A2 | 7/1997 |
| EP | 1 040 845 A | 10/2000 |
| JP | 3-62113 | 9/1991 |
| JP | 4-200566 | 7/1992 |
| JP | 3066107 | 11/1999 |
| WO | 95/03841 A | 2/1995 |
| WO | 99/24108 A | 5/1999 |

* cited by examiner

Primary Examiner—Brian L. Casler
Assistant Examiner—Cris L. Rodriguez
(74) Attorney, Agent, or Firm—Merchant & Gould P.C.

(57) ABSTRACT

A mixing/charging port for medical treatment in which no air bubble is retained inside thereof even at the time of priming, and which is capable of infusing a drug solution or transfusing blood into a patient safely. The mixing/charging port for medical treatment includes a disk-like valve having an insertion hole at the center, a seating for supporting the lower part of the periphery of the valve with the center of the rear surface side of the valve left unsupported, and a cover for restraining the valve by covering at least the upper part of the periphery of the valve with the center of the front surface side of the valve left uncovered, wherein: a fitting hole defined by an inner edge portion of the cover works as an anchor for anchoring an insertion member to the mixing/charging port in a way in which the insertion member is fitted to the fitting hole when the insertion member is inserted into the insertion hole; and the bottom surface of an opening part of a passage is located at a lower level relative to the inner bottom surface of the seating.

6 Claims, 5 Drawing Sheets

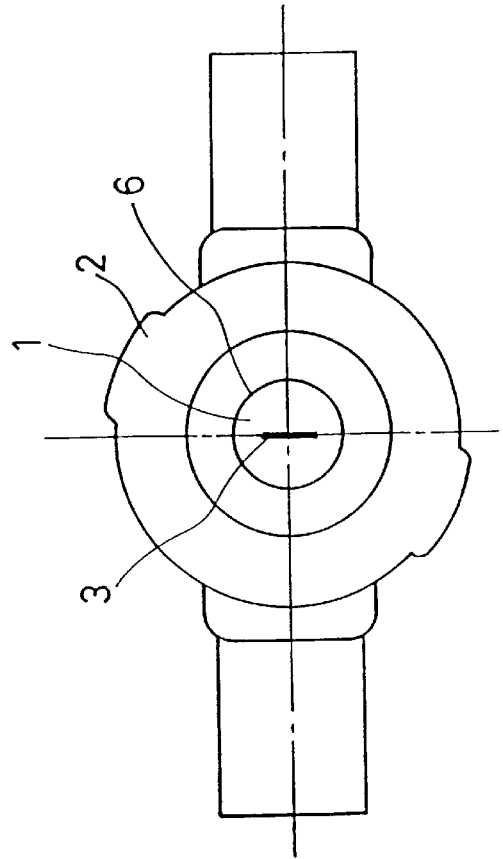
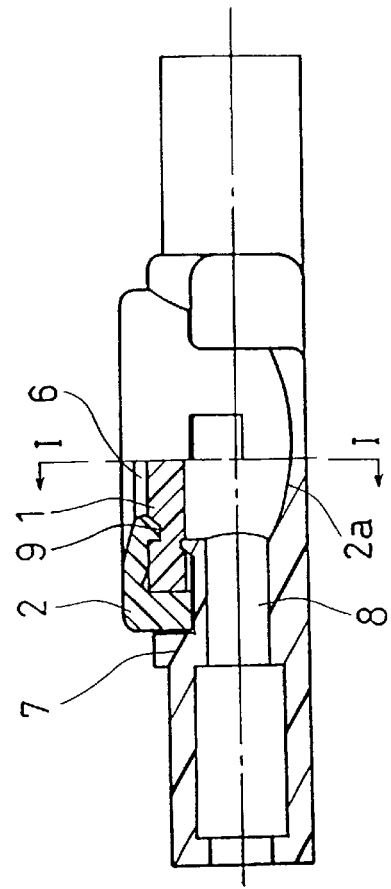
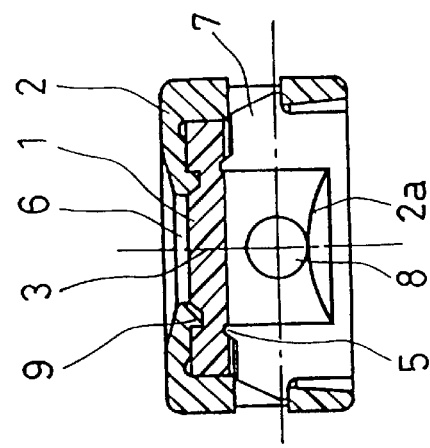
FIG. 1C (PRIOR ART)
FIG. 1A (PRIOR ART)
FIG. 1B (PRIOR ART)

MIXING/CHARGING PORT FOR MEDICAL TREATMENT

BACKGROUND OF THE INVENTION

1. Field of the Invention

The present invention relates to a mixing/charging port for medical treatment, which is placed on a medical instrument to make it easy and reliable to mix/charge solutions from the outside of a feeding passage or, on the other hand, to collect solutions from the inside of the feeding passage.

2. Description of the Prior Art

In infusing a drug solution or transfusing blood into a patient, it is often necessary to provide a main feeding passage with a side-infusing line in order to mix/charge different kinds of drug solutions or to collect the liquid flowing in the feeding passage as a sample. Conventionally, in this case, a feeding passage of an infusion set provided with a rubber mixing/charging port (cock) for piercing by needles is used and solutions are mixed/charged by piercing the mixing/charging port with an injection needle, etc.

However, in such a method, when piercing the site other than the predetermined piercing site of the mixing/charging port with the needle, the liquid may leak from the site. Another problem is that the injection needle may be contaminated due to a working error, etc. In order to fix and hold a luer, etc. to be inserted ("an insertion member" will be referred to hereinafter), recently, the mixing/charging port capable of holding an insertion member has been considered. An example includes a mixing/charging port equipped with a valve that opens when a male luer located at the tip of a syringe is inserted into the mixing/charging port to push the valve and which closes by itself when the luer is pulled out from the mixing/charging port.

However, in such a mixing/charging port, it is necessary to hold a luer at the mixing/charging port regardless of the state in which the valve is inserted (i.e., valve opens) or the state in which the valve is pulled out (i.e., valve closes). Therefore, there are the following various problems. More specifically, first, it is necessary to deepen a luer receiving part of the mixing/charging port. With such a shape, it is difficult to remove the liquid leaking from the valve, which easily may become unsanitary. Furthermore, in the mixing/charging port having such a deep luer receiving part, the liquid may begin to be mixed/charged in a state in which the luer is not sufficiently inserted into the valve. In this case, if the amount of drug solution to be mixed/charged is small, the administration of an effective amount of drug solution may not be carried out. Secondly, the structure of the valve becomes complicated, which may lead to increasing cost. Furthermore, as the structure of the valve is more complicated, failures are more likely to occur, and the valve is more likely to be broken.

On the other hand, in the conventional simple-structured mixing/charging port (for example, a mixing/charging port merely equipped with a disk-like valve made of an elastic member having a slit), it was difficult to insert a luer of a syringe into the mixing/charging port. If possible, it was difficult to hold the syringe reliably at the mixing/charging port. This is because the conventional disk-like valve is formed of a material having a large elasticity and has a simple structure in which the thick main body is merely provided with a slit, so that the valve is exhibits a large resistance when the luer is inserted into the valve, and the valve is deformed largely when the valve holds the luer. However, if the thickness of the elastic member is reduced or a material having a small elasticity is used in order to reduce the resistance when the luer is inserted, the backflow prevention effect of the valve is lowered, which may cause liquid leaking.

In order to solve the above-mentioned problems, there has been a proposal of a mixing/charging port for medical treatment having a simple structure and capable of reliably holding an insertion member, which includes a disk-like valve having an insertion hole at the center, a seating for supporting the lower part of the periphery of the valve with the center of the rear surface side of the valve left unsupported, a cover for restraining the valve by covering at least the upper part of the periphery of the valve with the center on the front surface side of the valve left uncovered, and an anchor means for anchoring the insertion member to the mixing/charging port by inserting the insertion member into the insertion hole and by using the edge portion of the cover provided with a fitting hole.

FIGS. 1A, 1B and 1C are projection drawings from three directions of an example of a conventional mixing/charging port for medical treatment. That is, FIG. 1A is a longitudinal sectional view of a mixing/charging port; FIG. 1B is a cross sectional view of the mixing/charging port along line I—I in FIG. 1A; and FIG. 1C is a plan view of the mixing/charging port, respectively.

In FIG. 1, reference numeral 1 denotes a disk-like valve, 2 denotes a cover, and 3 denotes an insertion hole. Furthermore, reference numeral 5 denotes an annular rib, 6 denotes a fitting hole, 7 denotes a seating, 2a denotes an inner bottom surface of seating 7, 8 denotes a passage, and 9 denotes a hook. In this structure, the valve 1 is sandwiched between the hook 9 and the cover 2 and the annular rib 5.

However, in the above-mentioned mixing/charging port for medical treatment, there has been a problem in that when priming of the inner part of the mixing/charging port is carried out, air bubbles may be present in some parts such as a cavity of the bottom surface of the mixing/charging port proper, a difference in level between the bottom surface and an opening part of the main route, a connection part between the mixing/charging port proper and a small-diameter tube, or the like. The occurrence of parts in which air bubbles are present makes it impossible to carry out the priming sufficiently, which may lead to a problem in that transfusion of blood or infusion of a drug solution into the vessel of a patient cannot be carried out safely.

For example, when priming a conventional mixing/charging port for medical treatment, air bubbles tend to be present in regions A and B as shown in FIG. 2, which is a cross sectional view of a conventional mixing/charging port for medical treatment. More specifically, the region A indicates a cavity of the bottom surface of the mixing/charging port proper, and the region B indicates a difference in level between the bottom surface and the opening part of the main route.

Furthermore, since the priming is carried out with the mixing/charging port turned upside down at a pressure of, for example, about 300 mmHg, air bubbles tend to be present in the regions A, B and C as shown in FIG. 3, which is a longitudinal sectional view showing the mixing/charging port during the priming. The regions A and B are the same as those shown in FIG. 2, and the region C is a connection part between the mixing/charging port proper and a small-diameter tube 10. Because the priming is carried out with the mixing/charging port turned upside down, FIG. 3 is a drawing inverted to show the mixing-charging port upside down.

SUMMARY OF THE INVENTION

With the foregoing in mind, it is an object of the present invention to provide a mixing/charging port for medical treatment in which air bubbles are not present even at the time of priming and which is capable of infusing a drug solution or transfusing blood into a patient safely.

In order to achieve the above-mentioned object, a mixing/charging port for medical treatment of the present invention includes a disk-like valve having an insertion hole at the center, a seating for supporting the lower part of the periphery of the valve with the center of the rear surface side of the valve left unsupported, and a cover for restraining the valve by covering at least the upper part of the periphery of the valve with the center of the front surface side of the valve left uncovered, wherein a fitting hole defined by an inner edge portion of the cover works as an anchor for anchoring an insertion member to the mixing/charging port in a way in which the insertion member is fitted to the fitting hole when the insertion member is inserted into the insertion hole; and the bottom surface of an opening part of a passage is located at a lower level relative to the inner bottom surface of the seating.

With such a configuration, since a cavity itself is eliminated from the bottom surface of the mixing/charging port main body and no difference in level occurs between a main stream of flow and the opening part of the passage, the flow is not made to be turbulent (i.e., turbulent flow does not occur). Thus, it is possible to prevent air bubbles from occurring. Furthermore, even if air bubbles occur due to a working error, etc., since there is no space for air bubbles to be able to be retained, such air bubbles easily can be ejected from the inside of the mixing/charging port.

Furthermore, in the mixing/charging port for medical treatment of the present invention, it is preferable that the passage is circular in cross section and the inner bottom surface of the seating is provided with a concave part having a shape in cross section that is the same as a shape defined by a chord and an arc located in a lower part of the opening part of the passage. It is preferable because the resident air bubbles are removed easily and also the passage for infusing liquid can be secured when the insertion member is inserted into the valve.

Furthermore, in the mixing/charging port for medical treatment of the present invention, it is preferable that the inner bottom surface of the seating is provided with a curved part of the bottom continuously connecting the inner side surface to the inner bottom surface of the seating. It is preferable because it is possible to allow the flow during the priming to be smoother and to suppress the occurrence of the turbulent flow more efficiently.

Furthermore, in the mixing/charging port for medical treatment of the present invention, it is preferable that any one side of the opening parts of the passage of the mixing/charging port is connected to a tube with a diameter smaller than the diameter of the opening part of the passage via a joint having a funnel shape in which the inner diameter gradually is reduced. It is preferable because it is possible to avoid the generation of turbulent flow due to the difference in diameter in the vicinity of the outlet of priming, thus to prevent air bubbles from occurring in the vicinity of the outlet of flow.

BRIEF DESCRIPTION OF THE DRAWINGS

FIG. 1A is a longitudinal sectional view of a conventional mixing/charging port;

FIG. 1B is a cross sectional view of the mixing/charging port along line I—I in FIG. 1A; and FIG. 1C is a conventional plan view of the mixing/charging port.

DESCRIPTION OF THE PREFERRED EMBODIMENTS

Figure 2:
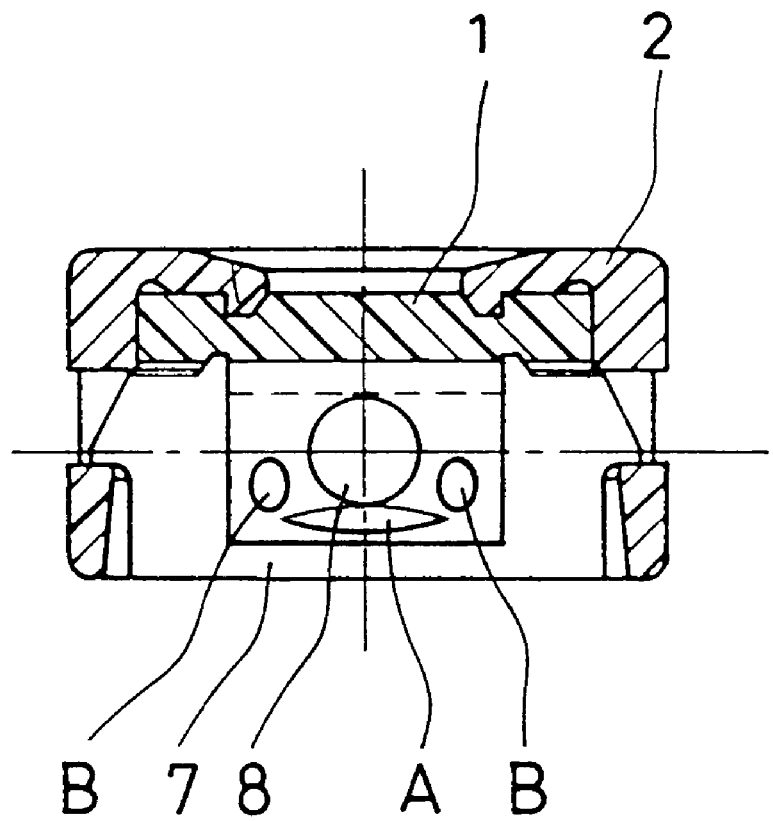
FIG. 2 is a cross-sectional view showing a conventional mixing/charging port for medical treatment.
Figure 3:
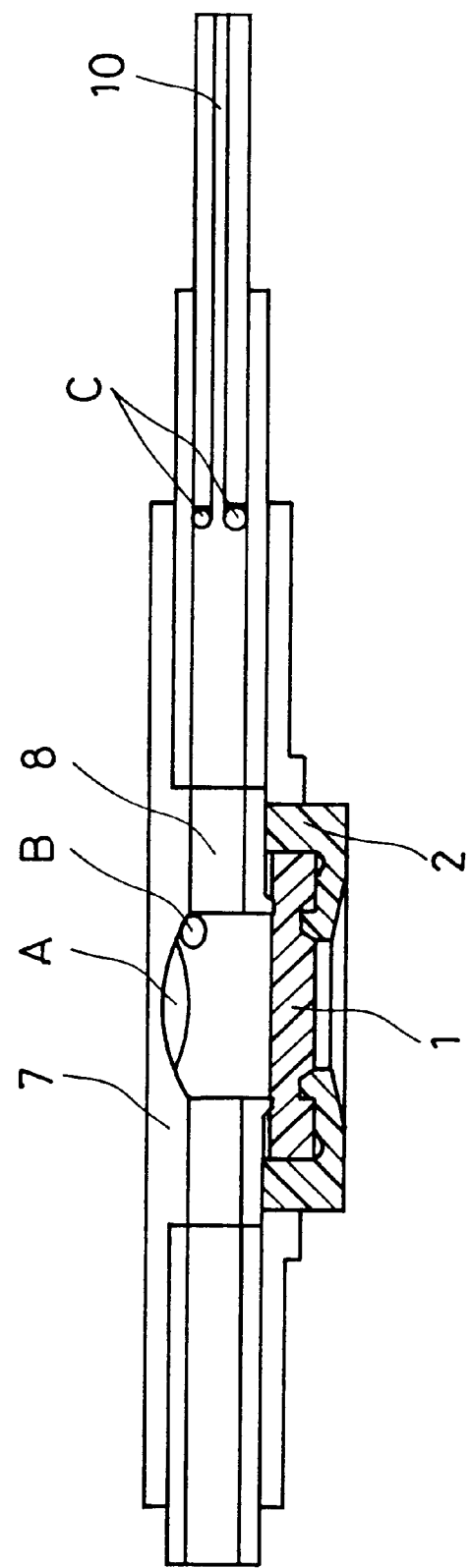
FIG. 3 is a longitudinal sectional view showing a conventional mixing/charging port for medical treatment.
Figure 4:
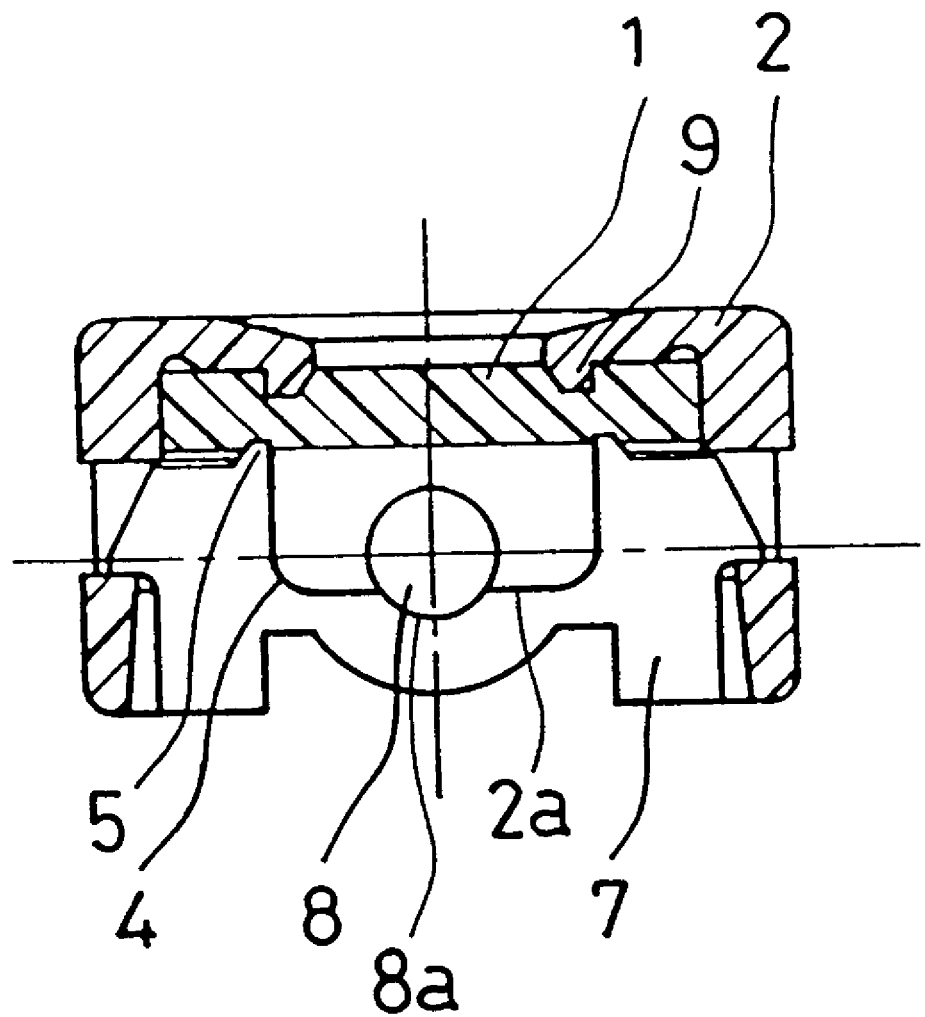
FIG. 4 is a cross-sectional view showing a mixing/charging port for medical treatment of an embodiment according to the present invention.

Hereinafter, the mixing/charging port for medical treatment of the present invention will be described by way of embodiments with reference to the accompanying drawings. FIG. 4 is a cross-sectional view showing a configuration of a mixing/charging port for medical treatment of this embodiment of the present invention. In FIG. 4, reference numeral 5 denotes an annular rib, 7 denotes a seating, 8 denotes a passage and 9 denotes a hook. The mixing/charging port for medical treatment of FIG. 4 is the same as in FIG. 1 in that the valve 1 is sandwiched between the hook 9 of the cover 2 and the annular rib 5.

The mixing/charging port for medical treatment of FIG. 4 is different from that of FIG. 1 in the location relationship between the passage 8 and the seating 7. More specifically, in the conventional mixing/charging port of FIG. 1, the bottom surface of the passage 8 is located at a level above the inner bottom surface of the seating 7, whereas in FIG. 4, the bottom surface of the passage 8 is located at a level below the inner bottom surface of the seating 7. Furthermore, in FIG. 4, the cavity of the inner bottom surface of the seating 7 is allowed to correspond to the shape of the bottom surface of the passage 8.

By locating the bottom surface of the passage 8 at a lower level than the inner bottom surface of the seating 7, a cavity that was present in the bottom surface of the mixing/charging port is eliminated. Thereby, it is possible to prevent the formation of air bubbles, which tend to occur in the cavity.

Furthermore, the inner bottom surface of the seating 7 is provided with a groove 8a having a shape obtained by cutting off the inner bottom surface of the seating 7 with the shape of the passage 8, in which the cross section of the groove 8a has a shape surrounded by a chord and an arc that are located in a lower part of the cross section of the passage 8. Therefore, no difference in level occurs between the opening part of the passage 8 and the inner bottom surface of the seating 7. Therefore, it is possible to prevent air bubbles from being generated by the occurrence of turbulent flow when flow collides with the position of a difference in level. In addition, it is possible to secure the passage for infusing liquid when the insertion member is inserted into the mixing/charging port.

Furthermore, even if air bubbles are generated due to a working error, etc., if only the priming is carried out with the mixing/charging port turned upside down, there is no space for air bubbles to be able to be retained. Therefore, it is possible to allow such air bubbles to be ejected to the outside of the mixing/charging port easily by the priming.

From the viewpoint of the manufacturing cost, it is preferable that the inner bottom surface of the seating 7 is provided with a groove 8a formed by uniformly cutting out the inner bottom surface of the seating 7 with the shape of passage 8. However, in order to minimize the amount of the resident air bubbles, it is more preferable that the bottom of the groove 8a corresponds to the bottom surface of the seating 7 at the center of the mixing/charging port and is cut out gradually deeper toward the both sides of the opening portion of the passage.

Furthermore, at the inner bottom surface of the seating 7, the inner side surface and the bottom surface may be connected continuously with a generally curved surface so as not to form a sharp corner on the inner bottom surface of the seating 7. By providing such a curved part of the bottom 4, it is possible to suppress the occurrence of turbulent flow more efficiently. Furthermore, it is possible to reduce the generation of air bubbles more efficiently as well as to reduce space for air bubbles to be able to be retained.

Figure 5:
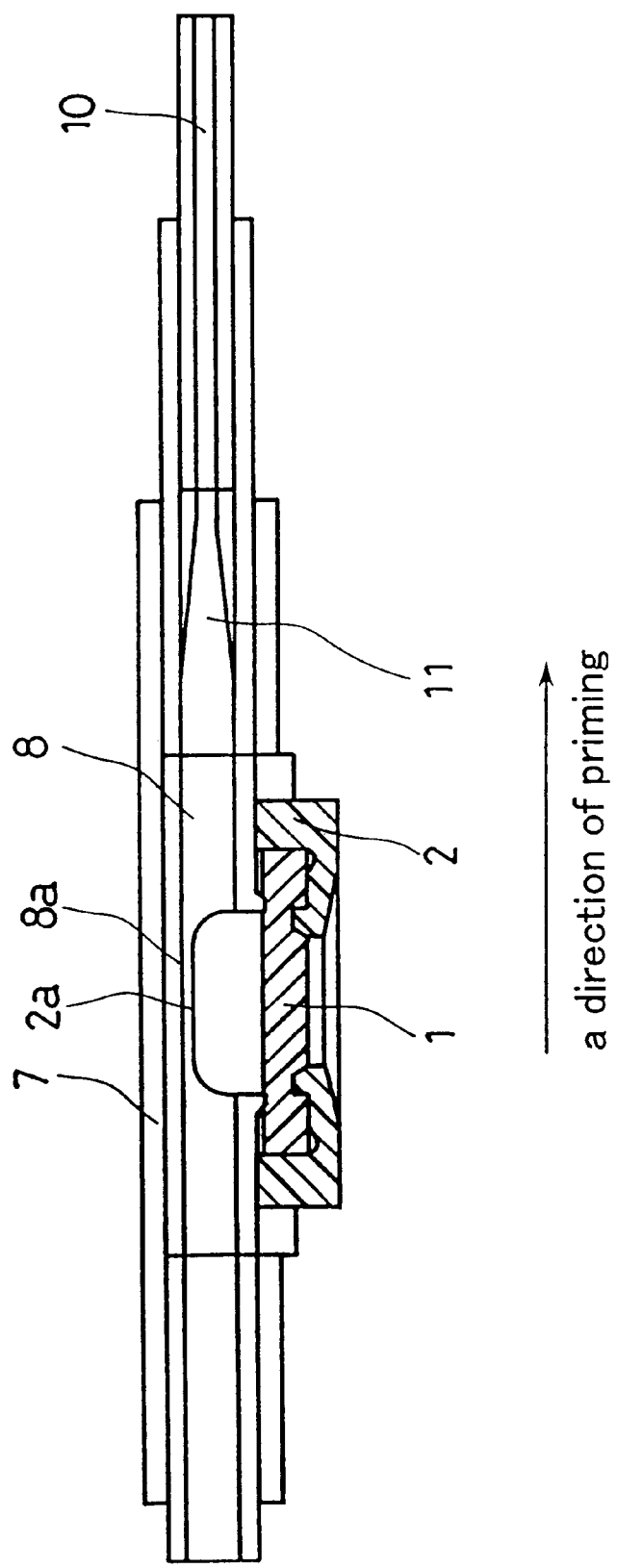
FIG. 5 is a longitudinal sectional view showing a mixing/charging port for medical treatment of an embodiment according to the present invention.

FIG. 5 is a cross sectional view showing a mixing/charging port for medical treatment of this embodiment according to the present invention. Since priming is carried out with the mixing/charging port turned upside down, FIG. 5 is a drawing inverted to show the mixing-charging port upside down.

In FIG. 5, the bottom surface (the upper part in FIG. 5) of the passage 8 is located at a lower level relative to the inner bottom surface (the upper part in FIG. 5) of the seating 7, and no difference in level occurs between the main route of flow and the opening part of the passage 8. Moreover, in the upper surface (the lower part in FIG. 5) of the passage 8, a difference in level occurs between the main route of flow and the opening part of the passage 8. However, since liquid is filled in a state in which the mixing/charging port is turned upside down, air bubbles generated herein easily can be ejected to the outside by the priming.

With such a configuration, since the bottom surface of the passage 8 is located at a lower level relative to the inner bottom surface of the seating 7, it is possible to prevent air bubbles from being retained in the cavity of the bottom surface of the mixing/charging port proper. Furthermore, since no difference in level occurs between the main route of flow and the opening part of the passage 8, a smoother flow can be achieved and also the generation of air bubbles due to the occurrence of turbulent flow can be suppressed.

Furthermore, in order to prevent air bubbles from being retained in the connection part between the passage 8 and a small-diameter tube at the outlet port of the priming, a joint 11 having a funnel shape with a gradually reducing diameter may be provided. By providing such a joint 11, liquid is allowed to flow smoothly and the occurrence of turbulent flow caused by the collision of flow is less likely to occur. Thus, the generation of air bubbles can be prevented and the occurrence and retention of air bubbles can be avoided.

Since no air bubbles are retained, it is possible to avoid the risk in that air bubbles are infused into the patient when transfusing blood or infusing a drug solution is carried out. Therefore, a medical treatment can be carried out safely.

Moreover, it is more preferable that the joint 11 is provided at the outlet side of the priming. It is preferable because air bubbles tend to occur when a difference in level is present at the outlet side, and the air bubble contaminated into the mixing/charging port proper can be ejected to the outside more smoothly.

The invention may be embodied in other forms without departing from the spirit or essential characteristics thereof. The embodiments disclosed in this application are to be considered in all respects as illustrative and not limitative, the scope of the invention is indicated by the appended claims rather than by the foregoing description, and all changes which come within the meaning and range of equivalency of the claims are intended to be embraced therein.

What is claimed is:

1. A mixing/charging port for medical treatment comprising a disk-shaped valve having an insertion hole at the center, a seating for supporting a lower part of the periphery of the valve with the center of a rear surface side of the valve left unsupported, the seating being capable of being interposed in a feeding passage so as to form a part of the feeding passage with an inner surface thereof, a cover for restraining the valve by covering at least an upper part of the periphery of the valve with the center of the front surface side of the valve left uncovered, and opening parts provided at a side wall of the seating so as to pass through the side wall of the seating, the opening parts being capable of being connected to the feeding passage, wherein:

a fitting hole defined by an inner edge portion of the cover acts as an anchor for anchoring an insertion member to the mixing/charging port so that the insertion member is fitted to the fitting hole when the insertion member is inserted into the insertion hole; and a bottom surface of the opening parts are located at a lower level relative to an inner bottom surface of the seating.

2. The mixing/charging port for medical treatment according to claim 1, wherein the passage is circular in cross section and the inner bottom surface of the seating is provided with a concave part having a shape in cross section that is the same as a shape defined by a chord and an arc located in a lower part of the opening part of the passage.

3. The mixing/charging port for medical treatment according to claim 1, wherein the inner bottom surface of the seating is provided with a curved part of the bottom continuously connecting an inner side surface to the inner bottom surface of the seating.

4. The mixing/charging port for medical treatment according to claim 1, wherein any one side of the opening parts of the passage of the mixing/charging port is connected to a tube with a diameter smaller than the diameter of the opening part of the passage via a joint having a funnel shape in which the inner diameter gradually is reduced.

5. The mixing/charging port for medical treatment according to claim 2, wherein any one side of the opening parts of the passage of the mixing/charging port is connected to a tube with a diameter smaller than the diameter of the opening part of the passage via a joint having a funnel shape in which the inner diameter gradually is reduced.

6. The mixing/charging port for medical treatment according to claim 3, wherein any one side of the opening parts of the passage of the mixing/charging port is connected to a tube with a diameter smaller than the diameter of the opening part of the passage via a joint having a funnel shape in which the inner diameter gradually is reduced.

* * * * *